(12) United States Patent
Baker et al.

(10) Patent No.: US 8,877,956 B2
(45) Date of Patent: Nov. 4, 2014

(54) 1,3,2-DIOXAPHOSPHORINANE, 2-SULFIDE DERIVATIVES FOR USE AS ANTI-WEAR ADDITIVES IN LUBRICANT COMPOSITIONS

(71) Applicant: Afton Chemical Corporation, Richmond, VA (US)

(72) Inventors: John Marshall Baker, Bracknell (GB); Naresh Mathur, Midlothian, VA (US); Roger M. Sheets, Pagosa Springs, CO (US); David J. Degonia, Midlothian, VA (US)

(73) Assignee: Afton Chemical Corporation, Richmond, VA (US)

(*) Notice: Subject to any disclaimer, the term of this patent is extended or adjusted under 35 U.S.C. 154(b) by 0 days.

(21) Appl. No.: 14/075,063

(22) Filed: Nov. 8, 2013

(65) Prior Publication Data

US 2014/0066646 A1 Mar. 6, 2014

Related U.S. Application Data

(62) Division of application No. 13/888,560, filed on May 7, 2013, now Pat. No. 8,618,030, which is a division of application No. 12/028,878, filed on Feb. 11, 2008, now Pat. No. 8,466,096.

(60) Provisional application No. 60/914,162, filed on Apr. 26, 2007.

(51) Int. Cl.
| | |
|---|---|
| *C07F 9/6571* | (2006.01) |
| *C10M 137/10* | (2006.01) |
| *G01N 33/30* | (2006.01) |
| *C10M 137/02* | (2006.01) |

(52) U.S. Cl.
CPC .......... *C10M 137/02* (2013.01); *C10N 2230/06* (2013.01); *C07F 9/657118* (2013.01); *C10M 2223/047* (2013.01); *C10M 137/105* (2013.01); *G01N 33/30* (2013.01); *C10N 2240/04* (2013.01); *C07F 9/657136* (2013.01); *C10N 2230/08* (2013.01)
USPC .............................................. 558/79; 558/86

(58) Field of Classification Search
CPC ...................................................... C07F 9/6571
USPC .................... 508/422, 287; 73/53.05; 568/12; 558/79, 86
See application file for complete search history.

(56) References Cited

U.S. PATENT DOCUMENTS

| | | | |
|---|---|---|---|
| 3,192,162 A | 6/1965 | Bartlett et al. | |
| 3,682,819 A | 8/1972 | Morris et al. | |
| 3,845,168 A | 10/1974 | Cuttag et al. | |
| 3,846,317 A | 11/1974 | Lintzenich et al. | |
| 4,778,613 A | 10/1988 | Cherney et al. | |
| 4,876,374 A * | 10/1989 | Adams et al. | 558/109 |
| 2006/0073992 A1 | 4/2006 | Dong et al. | |
| 2007/0142237 A1 | 6/2007 | DeGonia et al. | |

FOREIGN PATENT DOCUMENTS

| | | |
|---|---|---|
| GB | 823086 | 11/1959 |
| GB | 1268562 | 3/1972 |
| GB | 1293245 | 10/1972 |
| GB | 1329978 | 9/1973 |

OTHER PUBLICATIONS

Oswald, Synthesis of Cyclic Phosphorous Acid Esters by Transesterification, Can J. Chem. vol. 37 (1959), 1498-1504, Ontario, Canada.

Mikolajczyk et al., StereoChemistry of Organophosphorous Cyclic Compounds,, Tetrahedron, vol. 28, 1972, pp. 5411-5422.

* cited by examiner

*Primary Examiner* — Prem C Singh
*Assistant Examiner* — Chantel Graham
(74) *Attorney, Agent, or Firm* — Luedeka Neely Group, P.C.

(57) ABSTRACT

The present disclosure relates to a non-acidic, sulfur-containing, phosphorus-containing compound of the formula I

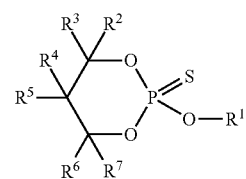

where $R^1$, $R^2$, $R^3$, $R^4$, $R^5$, $R^6$, and $R^7$ are as defined herein. Such a compound may exhibit improved antiwear performance and thermal stability in lubricating compositions.

2 Claims, No Drawings

1,3,2-DIOXAPHOSPHORINANE, 2-SULFIDE DERIVATIVES FOR USE AS ANTI-WEAR ADDITIVES IN LUBRICANT COMPOSITIONS

CROSS-REFERENCE TO RELATED APPLICATIONS

This application is a divisional application of copending application Ser. No. 13/888,560, filed May 7, 2013, which in turn is a divisional application of application Ser. No. 12/028,878, filed Feb. 11, 2008. This application also claims the benefit of the earlier filing date of provisional application Ser. No. 60/914,162, filed Apr. 26, 2007.

TECHNICAL FIELD

This disclosure relates to lubricant additives that may be used in a lubricating fluid having satisfactory anti-wear characteristics without detrimental surface and toxicological effects. The disclosure also relates to the preparation of such lubricant additives and concentrates containing such lubricant additives, as well as devices lubricated with a lubricating fluid that includes such lubricant additives.

BACKGROUND

The use of sulfur and phosphorus-containing compounds as anti-wear additives in lubricant compositions is known. In general, the sulfur and phosphorus-containing compounds comprise alkyl acid phosphates, alkyl acid thiophosphates, alkyl acid dithiophosphates, and their amine or metal salts. For example, zinc dialkyldithiophosphate (ZDDP) is a well-known sulfur and phosphorus-containing anti-wear agent. Because zinc is an environmental contaminant, the industry is under pressure to find novel metal-free (i.e. ashless) antiwear additives. In addition, because these compounds have acidic functionality, the compounds may actually attack the surface of the metal parts being lubricated and thus cause greater wear or corrosion.

As automobile manufacturers continue to make larger trucks with more powerful engines the amount of torque applied to the axles of these vehicles has increased enormously. Accordingly, the Original Equipment Manufacturers (OEM) have placed increased demands on the lubricant industry to address the increase in torque and extend axle life. In particular, what is needed is a lubricant composition having improved antiwear, thermal stability, and oxidative stability. Furthermore, there is needed a lubricant composition that can provide improved antiwear and thermal stability as evidenced by automotive screening tests such as the L-37 test ASTM D-6121.

Finally, a more recent problem attributed to known sulfur and phosphorus-containing antiwear compounds relates to their toxicity in lubricant compositions. Due to their acidic nature, such compounds may attack metal parts lubricated with fluids containing the compounds and thereby cause greater wear and/or corrosion. Accordingly, these compounds are typically neutralized with an oil-soluble amine. The neutralizing amines currently used for this purpose are particularly toxic, persistent and bioaccumulative. An amine-free, sulfur and phosphorus-containing compound is therefore desirable as an environmentally friendly alternative to today's anti-wear additives.

It has now been discovered that certain novel compounds as described below may be readily formulated into lubricating compositions to afford a unique solution for providing desired lubricant performance characteristics, such as improved anti-wear performance and good thermal stability while maintaining a low toxicity environmental footprint.

SUMMARY

The present disclosure describes a novel lubricant additive that may be capable of being used at relatively high treatment rates, and that may meet the anti-wear requirements of Original Equipment Manufacturers (OEMs) worldwide, including in the U.S., Europe, Asia-Pacific, and Asia, as well as service fill applications. Such an additive may also have no acid functionality, good thermal stability, and low toxicity.

An embodiment of the present disclosure describes a novel sulfur and phosphorus-containing compound according to the formula I,

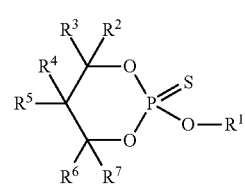

or an oil-soluble, tribologically acceptable salt, solvate, hydrate, or proadditive thereof;

wherein $R^1$, $R^2$, $R^3$, $R^4$, $R^5$, $R^6$, and $R^7$ are substituents independently selected from the group consisting of hydrogen (excluding $R^1$), $(C_1-C_6)$alkyl, $(C_1-C_6)$alkenyl, —$(C_3-C_7)$cycloalkyl, and —$(C_2-C_9)$heterocyclyl; wherein said $(C_1-C_6)$alkyl, —$(C_3-C_7)$cycloalkyl, and —$(C_2-C_9)$heterocyclyl; wherein said $(C_1-C_6)$alkyl, $(C_1-C_6)$alkenyl, —$(C_3-C_7)$cycloalkyl, and —$(C_2-C_9)$heterocyclyl substituents are optionally substituted by one to three moieties independently selected from the group consisting of hydrogen, halogen, hydroxyl, —$(C_1-C_{16})$alkyl, $(C_1-C_{16})$alkenyl, —CN, —$NR^8R^9$, —$(C_3-C_7)$cycloalkyl, —$(C_2-C_9)$heterocyclyl, —$CO_2R^{15}$, —$SO_2NR^8R^9$, $NR^{15}SO_2R^{10}$, —$SO_2R^{10}$ and —$CONR^8R^{11}$; wherein $R^8$ and $R^{11}$ of said —$CONR^8R^{11}$ group may be taken together with the atoms to which they are attached to form a —$(C_2-C_9)$heterocyclyl;

wherein $R^8$ and $R^9$ are each substituents independently selected from the group consisting of hydrogen, —$(C_1-C_6)$alkyl, —$(C_3-C_7)$cycloalkyl, —$(C_2-C_9)$heterocyclyl and said —$(C_2-C_9)$heterocyclyl group is optionally interrupted by one to three elements independently selected from the group consisting of —(C=O), —$SO_2$, —NH—, —$NR^{15}$, —$(C_6-C_{10})$aryl, —$(C_1-C_9)$heteroaryl, $COR^{15}$ and —$SO_2R^{15}$; wherein said —$(C_1-C_6)$alkyl, —$(C_3-C_7)$cycloalkyl, —$(C_2-C_9)$heterocyclyl, —$(C_6-C_{10})$aryl, —$(C_1-C_9)$heteroaryl, $COR^{15}$ and —$SO_2R^{15}R^8$ or $R^9$ substituents are optionally substituted by one to three moieties independently selected from the group consisting of hydrogen, halogen, chalcogen, —$CF_3$, —CN, —$(C_1-C_6)$alkyl, —$NH(C_1-C_6)$alkyl, —$NH(C_3-C_7)$cycloalkyl, —$NH(C_2-C_9)$heterocyclyl, —$NH(C_6-C_{10})$aryl, —$NH(C_1-C_9)$heteroaryl, —$N((C_1-C_6)$alkyl$)_2$, —$N((C_3-C_7)$cycloalkyl$)_2$-, —$N((C_2-C_9)$heterocyclyl$)_2$, —$N((C_6-C_{10})$aryl$)_2$, —$N((C_1-C_9)$heteroaryl$)_2$, —$O(C_1-C_6)$alkyl, —$O(C_3-C_7)$cycloalkyl, —$O(C_2-C_9)$heterocyclyl, —$O(C_6-C_{10})$aryl, —$O(C_1-C_9)$heteroaryl, —$(C_3-C_7)$cycloalkyl, —$(C_2-C_9)$heterocyclyl, —$CO_2R^{10}$, $SO_2NR^8R^9$, $NR^{15}SO_2R^{10}$, —$SO_2R^{10}$, —$CONH_2$, —$CONHR^{10}$, and —$CONR^{10}R^{11}$; wherein $R^{10}$ and $R^{11}$ of said —CONR$^{10}$R$^{11}$ group may be taken together with the nitrogen atom to which they are attached to form a —(C$_2$-C$_9$) heterocyclyl;

wherein R$^8$ and R$^9$ may be taken together with the atom(s) to which they are attached to form a —(C$_2$-C$_9$)heterocyclyl, wherein said —(C$_2$-C$_9$)heterocyclyl group is optionally substituted by one to three moieties selected from the group consisting of hydrogen, halogen, hydroxy, —CF$_3$, —NO$_2$, —CN, —(C$_r$C$_6$)alkyl, —(C$_2$-C$_6$)alkenyl, —(C$_2$-C$_6$)alkynyl, —C≡N—OH, —C≡N—O((C$_1$-C$_6$)-alkyl), —NR$^{10}$R$^{11}$, —OR$^{15}$, —(C$_3$-C$_7$)cycloalkyl, —(C$_2$-C$_9$)heterocyclyl, —CO$_2$R$^{15}$, —CONR$^{10}$R$^{11}$, —CONR$^9$R$^{11}$, —SR—SOR$^{10}$, —SO$_2$R$^{10}$, —SO$_2$NR$^{10}$R$^{11}$, —NHCOR$^{15}$, —NR$^{15}$CONR$^{10}$R$^{11}$, and —NR$^{12}$SO$_2$R$^{10}$, wherein said —(C$_2$-C$_6$)alkenyl and —(C$_2$-C$_6$)alkynyl moieties of said —(C$_2$-C$_9$)heterocyclyl group may be optionally substituted by one to three R$^{10}$ groups, and said —(C$_2$-C$_9$)heterocyclyl group is optionally interrupted by one to three elements independently selected from the group consisting of —(C═O), —SO$_2$, —NH—, and —NR$^{15}$;

wherein R$^{10}$ is a substituent selected from the group consisting of —(C$_1$-C$_6$)alkyl, —(C$_3$-C$_7$)cycloalkyl, —(C$_2$-C$_9$) heterocyclyl, —(C$_6$-C$_{10}$)aryl, and —(C$_1$-C$_9$) heteroaryl; wherein said —(C$_1$-C$_6$)alkyl, —(C$_3$-C$_7$)cycloalkyl, —(C$_2$-C$_9$)heterocyclyl, —(C$_6$-C$_{10}$)aryl, and —(C$_1$-C$_9$) heteroaryl R$^{10}$ substituents are optionally substituted by one to three moieties independently selected from the group consisting of hydrogen, halogen, hydroxy, —CN, —(C$_1$-C$_6$)alkyl, —NR$^{15}$, and —O(C$_1$-C$_6$)alkyl;

wherein R$^{11}$ is a substituent selected from the group consisting of hydrogen, —(C$_1$-C$_6$)alkyl, —(C$_3$-C$_7$)cycloalkyl, —(C$_2$-C$_9$)heterocyclyl, —(C$_6$-C$_{10}$)aryl, and —(C$_1$-C$_9$) heteroaryl; wherein said —(C$_1$-C$_6$)alkyl, —(C$_3$-C$_7$)cycloalkyl, —(C$_2$-C$_9$)heterocyclyl, —(C$_6$-C$_{10}$)aryl, and —(C$_1$-C$_9$) heteroaryl R$^{11}$ radicals are optionally substituted by one to three moieties independently selected from the group consisting of hydrogen, halogen, hydroxy, —CN, —(C$_1$-C$_6$)alkyl, —NH$_2$, —NHR$^{12}$, —NR$^{12}$$_2$, OR$^{12}$, —(C$_3$-C$_7$)cycloalkyl, —(C$_2$-C$_9$) heterocyclyl, —CO$_2$R$^{13}$, —CONH$_2$, —CONHR$^{13}$, and —CONR$^{13}$R$^{14}$; wherein R$^{13}$ and R$^{14}$ of —CONR$^{13}$R$^{14}$ may be taken together with the nitrogen atom to which they are attached to form a —(C$_2$-C$_9$)heterocyclyl;

wherein R$^{12}$ and R$^{13}$ are each independently, hydrogen, or —(C$_1$-C$_6$)alkyl; R$^{14}$ is hydrogen or —(C$_r$C$_6$)alkyl; and wherein R$^{15}$ is a substituent selected from the group consisting of hydrogen, —(C$_1$-C$_6$)alkyl, —(C$_3$-C$_7$)cycloalkyl, —(C$_2$-C$_9$)heterocyclyl, —(C$_6$-C$_{10}$)aryl, and —(C$_1$-C$_9$)heteroaryl; wherein said —(C$_1$-C$_6$)alkyl, —(C$_3$-C$_7$)cycloalkyl, —(C$_2$-C$_9$)heterocyclyl, —(C$_6$-C$_{10}$)aryl, and —(C$_1$-C$_9$)heteroaryl R$^{15}$ substituent is optionally substituted by one to three moieties independently selected from the group consisting of hydrogen, halogen, —CF$_3$, —CN, —(C$_1$-C$_6$)alkyl, —NH(C$_3$-C$_7$)cycloalkyl, —NH(C$_2$-C$_9$)heterocyclyl, —NH(C$_6$-C$_{10}$)aryl, —NH(C$_1$-C$_9$)heteroaryl, —N((C$_1$-C$_6$)alkyl)$_2$, —N((C$_3$-C$_7$)cycloalkyl)$_2$-, —N((C$_2$-C$_9$)heterocyclyl)$_2$, —N((C$_6$-C$_{10}$)aryl)$_2$, —N((C$_1$-C$_9$)heteroaryl)$_2$, —O(C$_3$-C$_7$) cycloalkyl, —(C$_2$-C$_9$)heterocyclyl, —O(C$_6$-C$_{10}$)aryl, —O(C$_1$-C$_9$)heterocyclyl, —(C$_3$-C$_7$)cycloalkyl, —(C$_2$-C$_9$)heterocyclyl, —CO$_2$R$^{10}$, —CONH$_2$, —CONHR$^{10}$, and —CONR$^{10}$R$^{11}$; wherein R$^{10}$ and R$^{11}$ of said —CONR$^{10}$R$^{11}$ group may be taken together with the atoms which they are attached to form a —(C$_2$-C$_9$) heterocyclyl.

In some embodiments, R$^1$ may represent ethyl.
In some embodiments, R$^4$ and R$^5$ may represent methyl.
In some embodiments, R$^1$ may represent oleyl.

In some embodiments, R$^1$ may represent a C$_1$-C$_6$ alkyl. Further, in some embodiments, said C$_1$-C$_6$ alkyl may be substituted with —OR$^8$.

In some embodiments, R$^8$ may be a —(C$_2$-C$_9$)heterocyclyl group.

In some embodiments R$^4$ and R$^5$ may represent butyl.
In some embodiments R$^6$ may represent isopropyl.
The following is a non-limiting list of compounds according to the present invention:

1,3,2-dioxaphosphorinane, 2,2'-[(2,2-dimethyl-1,3-propanediyl)bis(oxy)]bis[5,5-dimethyl-, 2,2'-disulfide;
1,3,2-dioxaphosphorinane, 5,5-dimethyl-2-(2-methylpropoxy)-, 2-sulfide;
1,3,2-dioxaphosphorinane, 5,5-dimethyl-2-oleoxy-, 2-sulfide;
1,3,2-dioxaphosphorinane, 2-(2-methoxyethoxy)-5,5-dimethyl-, 2-sulfide;
1,3,2-dioxaphosphorinane, 2-(cyclohexyloxy)-5,5-dimethyl-, 2-sulfide;
1,3,2-dioxaphosphorinane, 5-butyl-2-ethoxy-5-ethyl-, 2-sulfide;
1,3,2-dioxaphosphorinane, 2,2'-[1,6-hexanediylbis(oxy)]bis [5,5-dimethyl-, 2,2'-disulfide;
1,3,2-dioxaphosphorinane, 2-(allyloxy)-4-methyl-, 2-sulfide;
1,3,2-dioxaphosphorinane, 2-cetoxy, 2-sulfide;
1,3,2-dioxaphosphorinane, 4-(1,1-dimethylethyl)-2-methoxy-, 2-sulfide;
1,3,2-dioxaphosphorinane, 5-butyl-5-ethyl-2-(2-ethylhexyloxy)-, 2-sulfide;
1,3,2-dioxaphosphorinane, 2-methoxy-4-methyl-, 2-sulfide;
1,3,2-dioxaphosphorinane, 2-methoxy-5,5-dimethyl-, 2-sulfide;
1,3,2-dioxaphosphorinane, 2-methoxy-3-isopropyl-, 2-sulfide;
1,3,2-dioxaphosphorinane, 5,5-dimethyl-2-(2-propenyloxy)-, 2-sulfide;
1,3,2-dioxaphosphorinane, 2,2'-[1,4-cyclohexanediylbis (oxy)]bis[5,5-dimethyl-, 2,2'-disulfide;
1,3,2-dioxaphosphorinane, 2,2'-[1,2-ethanediylbis(oxy)]bis [5,5-dimethyl-, 2,2'-disulfide;
1,3,2-dioxaphosphorinane, 5,5-dimethyl-2-(1-methylethoxy)-, 2-sulfide;
1,3,2-dioxaphosphorinane, 5-(1,1-dimethylethyl)-2-methoxy-, 2-sulfide;
1,3,2-dioxaphosphorinane, 2-[(2,2-dimethyl-1,3-dioxolan-4-ylmethoxy]-4-methyl-, 2-sulfide; posphorothioic acid, cyclic OO-trimethylene O-2-propynyl ester;
1,3,2-dioxaphosphorinane, 2-ethoxy-, 2-sulfide;
1,3,2-dioxaphosphorinane, 2-methoxy-, 2-sulfide;
1,3,2-dioxaphosphorinane, 5-(1,1-dimethylethyl)-2-methoxy-, 2-sulfide;
1,3,2-dioxaphosphorinane, 5,5-dimethyl-2-propoxy-, 2-sulfide;
1,3,2-dioxaphosphorinane, 2-methoxy-4,6-dimethyl-, 2-sulfide;
1,3,2-dioxaphosphorinane, 2-(2-butenyloxy)-5,5-dimethyl-, 2-sulfide;
1,3,2-dioxaphosphorinane, 2-methoxy-5,5-dimethyl-, 2-sulfide;
1,3,2-dioxaphosphorinane, 2-ethoxy-5,5-dimethyl-, 2-sulfide;
ethanone, 2-[(4,4-dimethyl-2-oxido-1,3,2-dioxaphosphorinan-2-yl)thio]-1-(2-furanyl)-1-hexen-3-one,4-[(4,4-dimethyl-2-oxido-1,3,2-dioxaphosphorinan-2-yl)thio]-5-methyl-1-phenyl-,1,3,2-Dioxaphosphorinane, 2-(hexadecyloxy)-, 2-sulfide;

1,3,2-dioxaphosphorinane, 2-ethoxy-4-isopropyl-5,5-dimethyl, 2-sulfide;
1,3,2-dioxaphosphorinane, 2-ethoxy-5,5-dibutyl, 2-sulfide; and
a tribologically acceptable salt or solvate thereof.

In an embodiment, a lubricant composition may comprise one or more compounds according to formula I, or an oil-soluble, tribologically acceptable salt or solvate thereof.

In another embodiment, a lubricant additive composition may comprise one or more compounds according to formula I, or an oil-soluble, tribologically acceptable salt or solvate thereof.

In another embodiment, a lubricant composition may comprise a) a major amount of a base oil; and b) a minor amount of an additive composition comprising one or more compounds of formula I or an oil-soluble, tribologically acceptable salt or solvate thereof.

In another embodiment, the lubricant and lubricant additive compositions comprising one or more compounds of formula I, or a tribologically acceptable salt or solvate thereof, may further comprise one or more of the following: an air expulsion additive, an antioxidant, a corrosion inhibitor, a foam inhibitor, a metallic detergent, an oil-soluble ashless dispersant, an organic phosphorus compound, a seal-swell agent, a viscosity index improver, and an extreme pressure additive.

In some embodiments, a lubricant additive may comprise a reaction product obtained by the process of reacting 1,3-diols with trialkyl phosphites to produce an intermediate, reacting the intermediate with a suitable alcohol, and then with a sulfur source, to produce a compound of the present disclosure, having formula I.

In some embodiments, a method of lubricating a machine part may comprise lubricating said machine part with a lubricant composition including a compound of the formula I, or a tribologically acceptable salt or solvate thereof.

In some embodiments, lubricating a machine part with a compound of formula I further comprises lubricating machine parts selected from the group consisting of a gear, an axle, a differential, an engine, a crankshaft, a transmission, or a clutch.

In some embodiments, a method of lubricating a transmission with a compound of formula I further comprises lubricating a transmission selected from the group consisting of an automatic transmission, a manual transmission, an automated manual transmission, a semi-automatic transmission, a dual clutch transmission, a continuously variable transmission, and a toroidal transmission.

In some embodiments, a method of lubricating a transmission component with a compound of formula I further comprises lubricating a transmission component selected from the group consisting of a continuously slipping torque converter clutch, a slipping torque converter, a lock-up torque converter, a starting clutch, one or more shifting clutches, or an electronically controlled converter clutch.

In some embodiments, a method of lubricating a gear with a compound of formula I further comprises lubricating a gear selected from the group consisting of an automotive gear, a stationary gearbox, and an axle.

In some embodiments, a method of lubricating a gear with a compound of formula I further comprises lubricating a gear selected from the group consisting of a hypoid gear, a spur gear, a helical gear, a bevel gear, a worm gear, a rack and pinion gear, a planetary gear set, and an involute gear.

In some embodiments, a method of lubricating a differential with a compound of formula I further comprises lubricating a differential selected from the group consisting of a straight differential, a turning differential, a limited slip differential, a clutch-type limited slip differential, and a locking differential.

In some embodiments, a method of lubricating an engine with a compound of formula I further comprises lubricating an engine selected from the group consisting of an internal combustion engine, a rotary engine, a gas turbine engine, a four-stroke engine, and a two-stroke engine.

In some embodiments, a method of lubricating an engine with a compound of formula I further comprises lubricating an engine including a piston, a bearing, a crankshaft, and/or a camshaft.

Another embodiment includes a method for testing the lubricant properties of a composition using a testing apparatus comprising lubricating said testing apparatus with a lubricant composition comprising a compound of the formula I, or a tribologically acceptable salt or solvate thereof. The test apparatus may include a Brookfield viscometer, any Vickers Test apparatus, an SAE No. 2 friction test machine, an electric motor-driven Hydra-Matic 4L60-E automatic transmission, ASTM D 471 or D 676 Elastomer Compatibility test equipment, NOACK volatility procedure machine, any test apparatus necessary for ASTM D 2882, D 5182, D 4172, D3233, and D2782 Wear Procedures, ASTM Foaming Procedure apparatus, test apparatus necessary for ASTM D 130 Copper Corrosion test, test equipment specified by the International Harvester Procedure Method BT-9 Rust Control test, test apparatus required by ASTM D 892 Foaming test, test apparatus required by ASTM D 4998 Gear Anti-Wear Performance test, Link M1158 Oil/Friction Machine, L-33-1 Test Apparatus, L-37 Test Apparatus, L-42 Test Apparatus, L-60-1 Test Apparatus, Strama 4-Square Electric Motor-Driven Procedure Machine, FZG Test Apparatus and parts, SSP-180 Procedure Machine, test apparatus for ASTM D 5579 High Temperature Cyclic Durability Procedure, Sauer-Danfoss Series 22 or Series 90 Axial Piston Pump, John Deere Synchro-Plus transmission, an SRV-friction wear tester, a 4-ball test apparatus, an LFW-1 test apparatus, a sprag clutch over-running wear test (SCOWT) apparatus, API CJ-4 engine tests, L-33 Moisture Corrosion Test, High-Temperature Cyclic Durability Test (ASTM D 5579), 288-hour VE engine oil performance test, L-38 standard lubricant test, Denison P46 Piston Pump Test Stand, Sundstrand Dynamic Corrosion Test Stand, a block-on-ring test apparatus, and any test apparatus required for performing test analysis under Mercon®, Mercon®V, Dexron® III, Dexron® III-H, Caterpillar® TO-4, Allison® C-4, JASO, GF-4, GF-5, MIL-E, MIL-L, and Sequences II through VIII.

In another embodiment, a method for improving the anti-wear properties of a lubricating fluid may comprise including in a lubricating fluid an effective amount of one or more compounds of formula I, or a tribologically acceptable salt or solvate thereof.

In another embodiment, a method for improving the anti-wear properties of a lubricating fluid while lubricating an automotive component requiring lubrication may comprise 1) adding a lubricating fluid to an automotive component requiring lubrication, said fluid comprising (a) a base oil, and (b) one or more compounds of formula I, or a tribologically acceptable salt or solvate thereof; and 2) operating the automotive component that contains the fluid, wherein the anti-wear performance of the fluid is improved relative to the performance of a lubricating fluid free of the compound of 1)(b).

In another embodiment, a method of making a lubricant additive may comprise reacting a 1,3-diol with a trialkyl phosphite to form a 1,3,2-dioxaphosphorinane; and reacting the 1,3,2-dioxaphosphorinane with elemental sulfur or an organic sulfur compound to form a 2-sulfide-1,3,2-dioxaphosphorinane.

In another embodiment, a method of making a lubricant additive may comprise reacting a 1,3-diol with a trialkyl phosphite to form a 1,3,2-dioxaphosphorinane; reacting the 1,3,2-dioxaphosphorinane with an alcohol to form a reaction product; and reacting the reaction product with elemental sulfur or an organic sulfur compound to form a 2-sulfide-1,3,2-dioxaphosphorinane.

The disclosed process may include the use of solvents. The solvent may be any inert fluid substance in which at least one of the reactants is soluble or the product is soluble. Non-limiting examples include benzene, toluene, xylene, n-hexane, cyclohexane, naphtha, diethyl ether carbitol, dibutyl ether dioxane, chlorobenzene, nitrobenzene, carbon tetrachloride, chloroform, base oil, such as gas-to-liquid and polyalphaolefin, and process oil.

A compound of formula I, or a tribologically acceptable salt or solvate thereof may be made at about room temperature (23° C.) or above, for example at least about 50° C., and as a further example ranging from about 50° C. to about 150° C., and as an even further example, from about 100° C. to about 120° C.

A compound of formula I, or a tribologically acceptable salt or solvate thereof may be formed separately and then added to a lubricating or functional fluid composition. Alternatively, a compound of formula I, or a tribologically acceptable salt or solvate thereof may be formed when the phosphorus-containing compound, such as the disclosed phosphite, is blended, mixed and/or reacted with other components to form the lubricating or functional fluid composition.

A compound of formula I, or a tribologically acceptable salt or solvate thereof may be oil-soluble, i.e., the hydrocarbyl chain of $R^1$ may be of sufficient length, such as at least about six carbon atoms, so that the resultant compound is soluble in a formulated composition. The incorporation of hydrophobic groups may lead to an increase in solubility in a non-polar media.

In an aspect, a compound of formula I, or a tribologically acceptable salt or solvate thereof may be present in a lubricant composition in any amount effective to provide antiwear improvement. For example, the compound may be present in an amount ranging from about 0.1 to about 10 wt. %, for example from about 0.3 to about 8 wt. %, and as a further example from about 0.3 to about 6 wt. % relative to the total weight of the lubricant composition. As a further example, a compound of formula I, or a tribologically acceptable salt or solvate thereof may be present in an amount to provide about 150 ppm to 3000 ppm of phosphorus in a finished fluid.

In another embodiment, a lubricant composition may comprise a mixture of (a) a major amount of a lubricating oil; and (b) a minor amount of an additive composition, comprising a compound having the formula I,

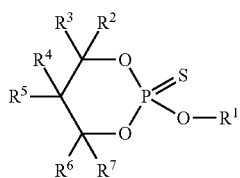

I or a tribologically acceptable salt, solvate, hydrate, or proadditive thereof;

wherein $R^1$, $R^2$, $R^3$, $R^4$, $R^5$, $R^6$, and $R^7$ are substituents independently selected from the group consisting of hydrogen, $(C_1-C_6)$alkyl, $(C_1-C_6)$alkenyl, —$(C_3-C_7)$cycloalkyl, and —$(C_2-C_9)$heterocyclyl; wherein said $(C_1-C_6)$alkyl, —$(C_3-C_7)$cycloalkyl, and —$(C_2-C_9)$heterocyclyl; wherein said $(C_1-C_6)$alkyl, $(C_1-C_6)$alkenyl, —$(C_3-C_7)$cycloalkyl, and —$(C_2-C_9)$heterocyclyl substituents are optionally substituted by one to three moieties independently selected from the group consisting of hydrogen, halogen, hydroxyl, —$(C_1-C_{16})$alkyl, $(C_1-C_{16})$alkenyl, —CN, —$NR^8R^9$, —$(C_3-C_7)$cycloalkyl, —$(C_2-C_9)$heterocyclyl, —$CO_2R^{15}$, —$SO_2NR^8R^9$, $NR^{15}SO_2R^{10}$, —$SO_2R^{19}$ and —$CONR^8R^{11}$; wherein $R^8$ and $R^{11}$ of said —$CONR^8R^{11}$ group may be taken together with the atoms to which they are attached to form a —$(C_2-C_9)$heterocyclyl;

wherein $R^8$ and $R^9$ are each substituents independently selected from the group consisting of hydrogen, —$(C_1-C_6)$alkyl, —$(C_3-C_7)$cycloalkyl, —$(C_2-C_9)$heterocyclyl and said —$(C_2-C_9)$heterocyclyl group is optionally interrupted by one to three elements independently selected from the group consisting of —(C=O), —$SO_2$, —NH—, —$NR^{15}$, —$(C_6-C_{10})$aryl, —$(C_1-C_9)$heteroaryl, $COR^{15}$ and —$SO_2R^{15}$; wherein said —$(C_1-C_6)$alkyl, —$(C_3-C_7)$cycloalkyl, —$(C_2-C_9)$heterocyclyl, —$(C_6-C_{10})$aryl, —$(C_1-C_9)$heteroaryl, $COR^{15}$ and —$SO_2R^{15}R^8$ or $R^9$ substituents are optionally substituted by one to three moieties independently selected from the group consisting of hydrogen, halogen, chalcogen, —$CF_3$, —CN, —$(C_1-C_6)$alkyl, —$NH(C_1-C_6)$alkyl, —$NH(C_3-C_7)$cycloalkyl, —$NH(C_2-C_9)$heterocyclyl, —$NH(C_6-C_{10})$aryl, —$NH(C_1-C_9)$heteroaryl, —$N((C_1-C_6)$alkyl$)_2$, —$N((C_3-C_7)$cycloalkyl$)_2$-, —$N((C_2-C_9)$heterocyclyl$)_2$, —$N((C_6-C_{10})$aryl$)_2$, —$N((C_1-C_9)$heteroaryl$)_2$, —$O(C_1-C_6)$alkyl, —$O(C_3-C_7)$cycloalkyl, —$O(C_2-C_9)$heterocyclyl, —$O(C_6-C_{10})$aryl, —$O(C_1-C_9)$heteroaryl, —$(C_3-C_7)$cycloalkyl, —$(C_2-C_9)$heterocyclyl, —$CO_2R^{10}$, $SO_2NR^9R^9$, $NR^{15}SO_2R^{10}$, —$SO_2R^{10}$, —$CONH_2$, —$CONHR^{10}$, and —$CONR^{10}R^{11}$; wherein $R^{10}$ and $R^{11}$ of said —$CONR^{10}R^{11}$ group may be taken together with the nitrogen atom to which they are attached to form a —$(C_2-C_9)$heterocyclyl;

wherein $R^8$ and $R^9$ may be taken together with the atom(s) to which they are attached to form a —$(C_2-C_9)$heterocyclyl, wherein said —$(C_2-C_9)$heterocyclyl group is optionally substituted by one to three moieties selected from the group consisting of hydrogen, halogen, hydroxy, —$CF_3$, —$NO_2$, —CN, —$(C_1-C_6)$alkyl, —$(C_2-C_6)$alkenyl, —$(C_2-C_6)$alkynyl, —C=N—OH, —C=N—O$((C_1-C_6)$-alkyl), —$NR^{10}R^{11}$, —$OR^{15}$, —$(C_3-C_7)$cycloalkyl, —$(C_2-C_9)$heterocyclyl, —$CO_2R^{15}$, —$CONR^{10}R^{11}$, —$CONR^9R^{11}$, —SR—$SOR^{10}$, —$SO_2R^{10}$, —$SO_2NR^{10}R^{11}$, —$NHCOR^{15}$, —$NR^{15}CONR^{10}R^{11}$, and —$NR^{12}SO_2R^{10}$, wherein said —$(C_2-C_6)$alkenyl and —$(C_2-C_6)$alkynyl moieties of said —$(C_2-C_9)$heterocyclyl group may be optionally substituted by one to three $R^{10}$ groups, and said —$(C_2-C_9)$heterocyclyl group is optionally interrupted by one to three elements independently selected from the group consisting of —(C=O), —$SO_2$, —NH—, and —$NR^{15}$;

wherein $R^{10}$ is a substituent selected from the group consisting of —$(C_1-C_6)$alkyl, —$(C_3-C_7)$cycloalkyl, —$(C_2-C_9)$heterocyclyl, —$(C_6-C_{10})$aryl, and —$(C_1-C_9)$heteroaryl; wherein said —$(C_1-C_6)$alkyl, —$(C_3-C_7)$cycloalkyl, —$(C_2-C_9)$heterocyclyl, —$(C_6-C_{10})$aryl, and —$(C_1-C_9)$heteroaryl $R^{10}$ substituents are optionally substituted by one to three moieties independently selected from the group consisting of hydrogen, halogen, hydroxy, —CN, —$(C_1-C_6)$alkyl, —$NR^{15}$, and —$O(C_1-C_6)$alkyl;

wherein $R^{11}$ is a substituent selected from the group consisting of hydrogen, —$(C_1-C_6)$alkyl, —$(C_3-C_7)$cycloalkyl, —$(C_2-C_9)$heterocyclyl, —$(C_6-C_{10})$aryl, and —$(C_1-C_9)$heteroaryl; wherein said —$(C_1-C_6)$alkyl, —$(C_3-C_7)$cycloalkyl, —$(C_2-C_9)$heterocyclyl, —$(C_6-C_{10})$aryl, and —$(C_1-C_9)$heteroaryl $R^{11}$ radicals are optionally substituted by one to three moieties independently selected from the group consisting of hydrogen, halogen, hydroxy, —CN, —$(C_1-C_6)$alkyl, —$NH_2$, —$NHR^{12}$, —$NR^{12}_2$, $OR^{12}$, —$(C_3-C_7)$cycloalkyl, —$(C_2-C_9)$heterocyclyl, —$CO_2R^{13}$, —$CONH_2$, —$CONHR^{13}$, and —$CONR^{13}R^{14}$; wherein $R^{13}$ and $R^{14}$ of —$CONR^{13}R^{14}$ may be taken together with the nitrogen atom to which they are attached to form a —$(C_2-C_9)$heterocyclyl;

wherein $R^{12}$ and $R^{13}$ are each independently, hydrogen, or —$(C_1-C_6)$alkyl;

wherein $R^{14}$ is hydrogen or —$(C_1-C_6)$alkyl; and wherein $R^{15}$ is a substituent selected from the group consisting of hydrogen, —$(C_1-C_6)$alkyl, —$(C_3-C_7)$cycloalkyl, —$(C_2-C_9)$heterocyclyl, —$(C_6-C_{10})$aryl, and —$(C_1-C_9)$heteroaryl; wherein said —$(C_1-C_6)$alkyl, —$(C_3-C_7)$cycloalkyl, —$(C_2-C_9)$heterocyclyl, —$(C_6-C_{10})$aryl, and —$(C_1-C_9)$heteroaryl $R^{15}$ substituent is optionally substituted by one to three moieties independently selected from the group consisting of hydrogen, halogen, —$CF_3$, —CN, —$(C_1-C_6)$alkyl, —$NH(C_1-C_6)$alkyl, —$NH(C_3-C_7)$cycloalkyl, —$NH(C_2-C_9)$heterocyclyl, —$NH(C_6-C_{10})$aryl, —$NH(C_1-C_9)$heteroaryl, —$N((C_1-C_6)$alkyl$)_2$, —$N((C_3-C_7)$cycloalkyl$)_2$-, —$N((C_2-C_9)$heterocyclyl$)_2$, —$N((C_6-C_{10})$aryl$)_2$, —$N((C_1-C_9)$heteroaryl$)_2$,—$O(C_1-C_6)$alkyl,—$O(C_3-C_7)$cycloalkyl,—$O(C_2-C_9)$heterocyclyl, —$O(C_6-C_{10})$aryl, —$O(C_1-C_9)$heteroaryl, —$(C_3-C_7)$cycloalkyl, —$(C_2-C_9)$heterocyclyl, —$CO_2R^{10}$, —$CONH_2$, —$CONHR^{10}$, and —$CONR^{10}R^{11}$; wherein $R^{10}$ and $R^{11}$ of said —$CONR^{10}R^{11}$ group may be taken together with the atoms which they are attached to form a —$(C_2-C_9)$ heterocyclyl.

In some embodiments, a lubricant composition may comprise a mixture of: (a) a major amount of a lubricating oil; and (b) an anti-wear improving effective amount of a thermally stable compound having the formula I.

The present disclosure may also include isotopically-labeled compounds, which are identical to those recited in formula I, but for the fact that one or more atoms are replaced by an atom having an atomic mass or mass number different from the atomic mass or mass number usually found in nature. Examples of isotopes that can be incorporated into compounds of the present disclosure include isotopes of hydrogen, carbon, nitrogen, oxygen, phosphorus, sulfur, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present disclosure, proadditives thereof, and tribologically acceptable salts of said compounds or of said proadditives which contain the aforementioned isotopes and/or other isotopes of other atoms are within the scope of the present disclosure. Phosphorus-31, i.e., $^{31}P$, and carbon-13, i.e., $^{13}Cl$, isotopes are particularly preferred for their ease of preparation and detectability. Isotopically-labeled compounds of formula I of the present disclosure and proadditives thereof can generally be prepared by carrying out the procedures disclosed by substituting a readily available isotopically-labeled reagent for a non-isotopically-labeled reagent.

The present disclosure also relates to the tribologically acceptable acid addition salts of compounds of the formula I. The acids which are used to prepare the tribologically acceptable acid addition salts of the aforementioned base compounds of the present disclosure are those which form acid addition salts, i.e., salts containing tribologically acceptable anions, such as the chloride, bromide, iodide, nitrate, sulfate, bisulfate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The present disclosure also relates to base addition salts of formula I. The chemical bases that may be used as reagents to prepare tribologically acceptable base salts of those compounds of formula I that are acidic in nature are those that form base salts with such compounds. Such base salts include, but are not limited to cations such as alkali metal cations (e.g., potassium and sodium) and alkaline earth metal cations (e.g., calcium and magnesium), ammonium or amine addition salts such as N-methylglucamine-(meglumine), and alkanolammonium and other base salts of tribologically acceptable organic amines.

The phrase "tribologically acceptable salt(s)," as used herein, unless otherwise indicated, includes salts of acidic or basic groups which may be present in the compounds of the present disclosure. The compounds of the present disclosure that are basic in nature may be capable of forming a wide variety of salts with various inorganic and organic acids. The acids that may be used to prepare tribologically acceptable acid addition salts of such basic compounds are those that form acid addition salts, i.e., salts containing tribologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds of the present disclosure that include a basic moiety, such as an amino group, may form tribologically acceptable salts with various amines, in addition to the acids mentioned above.

The present disclosure also encompasses lubricant or tribological compositions containing proadditives of compounds of the formula I. Compounds of formula I having free amino, amido, hydroxy or carboxylic groups can be converted into proadditives. Proadditives may include compounds wherein an amino residue, carbonates, carbamates, amides, alkyl esters, etc. are covalently bonded to the substituents of formula I but are sufficiently labile under typical lubricant use conditions that the proadditive yields a compound of formula I.

The present disclosure may also encompass compounds of formula I containing protective groups. One skilled in the art will also appreciate that compounds of the present disclosure can also be prepared with certain protecting groups that are useful for purification or storage and can be removed before use in the device to be lubricated. The protection and deprotection of functional groups is described in "Protective Groups in Organic Chemistry," edited by J. W. F. McOmie, Plenum Press (1973) and "Protective Groups in Organic Synthesis," 3rd edition, T. W. Greene and P. G. M. Wuts, Wiley-Interscience (1999).

The compounds of the present disclosure may include all stereoisomers (e.g., cis and trans isomers) and all optical isomers of compounds of the formula I (e.g., R and S enantiomers), as well as racemic, diastereomeric and other mixtures of such isomers.

The compounds, salts and proadditives of the present disclosure may exist in several tautomeric forms, including the enol and keto forms, or the imine and enamine forms, and geometric isomers and mixtures thereof. All such tautomeric forms are included within the scope of the present disclosure. Tautomers exist as mixtures of a tautomeric set in solution. In solid form, usually one tautomer predominates. Even though one tautomer may be described, the present disclosure includes all tautomers of the present compounds.

The present disclosure also includes atropisomers of the present disclosure. Atropisomers refer to compounds of formula I that may be separated into rotationally restricted isomers.

The compounds of the present disclosure may contain olefin-like double bonds. When such bonds are present, the compounds of the present disclosure may exist as cis and trans configurations and as mixtures thereof.

The term "interrupted by" refers to compounds in which a ring carbon atom is replaced by an element selected from the group consisting of —(C=O), —SO$_2$, —N=, —NH—, and —NR$^1$—. For example, if a substituent is —(C$_6$-C$_{10}$)aryl, such as

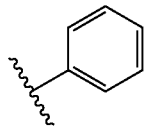 [SMILES: *c1ccccc1]

the ring may be interrupted or replaced by a nitrogen heteroatom to form the following ring:

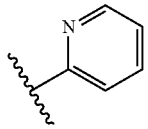 [SMILES: *c1ccccn1]

such that a ring carbon is replaced by the heteroatom nitrogen. Compounds of the present disclosure can accommodate up to three such replacements or interruptions.

A "suitable substituent" is intended to mean a chemically and tribologically acceptable functional group, i.e., a moiety that does not negate the tribological activity of the inventive compounds. Such suitable substituents may be routinely selected by those skilled in the art. Illustrative examples of suitable substituents include, but are not limited to, halo groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO—(C=O)— groups, amino groups, alkyl- and dialkylamino groups, carbamoyl groups, alkylcarbonyl groups, alkoxycarbonyl groups, alkylaminocarbonyl groups, dialkylamino carbonyl groups, arylcarbonyl groups, aryloxycarbonyl groups, alkylsulfonyl groups, arylsulfonyl groups and the like. Those skilled in the art will appreciate that many substituents can be substituted by additional substituents. Further examples of suitable substituents include those recited in the definition of compounds of formula I, including R$^1$ through R$^{15}$, as defined herein.

As used herein, the term "alkyl," as well as the alkyl moieties of other groups referred herein (e.g., alkoxy), may be linear or branched (such as methyl, ethyl, n-propyl, isopropyl, n-butyl, iso-butyl, secondary-butyl, tertiary-butyl); optionally substituted by 1 to 3 suitable substituents as defined above such as fluoro, chloro, trifluoromethyl, (C$_1$-C$_6$)alkoxy, (C$_6$-C$_{10}$)aryloxy, trifluoromethoxy, difluoromethoxy or (C$_1$-C$_6$)alkyl. The phrase "each of said alkyl" as used herein refers to any of the preceding alkyl moieties within a group such as alkoxy, alkenyl or alkylamino.

As used herein, the term "cycloalkyl" refers to a mono, bicyclic or tricyclic carbocyclic ring (e.g., cyclopropyl, cyclobutyl, cyclopentyl, cyclohexyl, cycloheptyl, cyclooctyl, cyclononyl, cyclopentenyl, cyclohexenyl, bicycloheptanyl, bicyclooctanyl and bicyclononanyl, etc.); optionally containing 1 or 2 double bonds and optionally substituted by 1 to 3 suitable substituents as defined above which includes but is not limited to fluoro, chloro, trifluoromethyl, (C$_1$-C$_6$)alkoxy, (C$_6$-C$_{10}$)aryloxy, trifluoromethoxy, difluoromethoxy or (C$_1$-C$_6$)alkyl.

As used herein, the term "halogen" includes fluoro, chloro, bromo, or iodo or fluoride, chloride, bromide, or iodide.

As used herein, the term "alkenyl" means straight or branched chain unsaturated radicals of 2 to 22 carbon atoms, including, but not limited to, ethenyl, 1-propenyl, 2-propenyl (allyl), iso-propenyl, 2-methyl-1-propenyl, 1-butenyl, 2-butenyl, and the like; optionally substituted by 1 to 3 suitable substituents as defined above which include but are not limited to fluoro, chloro, trifluoromethyl, (C$_1$-C$_6$)alkoxy, (C$_6$-C$_{10}$)aryloxy, trifluoromethoxy, difluoromethoxy or (C$_1$-C$_6$)alkyl.

As used herein, the term "alkynyl" is used herein to mean straight or branched hydrocarbon chain radicals having one triple bond including, but not limited to, ethynyl, propynyl, butynyl, and the like; optionally substituted by 1 to 3 suitable substituents as defined above which include but are not limited to fluoro, chloro, trifluoromethyl, (C$_1$-C$_6$)alkoxy, (C$_6$-C$_{10}$)aryloxy, trifluoromethoxy, difluoromethoxy or (C$_1$-C$_6$)alkyl.

As used herein, the term "carbonyl" or "(C=O)" (as used in phrases such as alkylcarbonyl, alkyl-(C=O)— or alkoxycarbonyl) refers to the joinder of the >C=O moiety to a second moiety such as an alkyl or amino group (i.e. an amido group). Alkoxycarbonylamino (i.e. alkoxy(C=O)—NH—) refers to an alkyl carbamate group. The carbonyl group is also equivalently defined herein as (C=O). Alkylcarbonylamino refers to groups such as acetamide.

As used herein, the term "aryl" means aromatic radicals which include but are not limited to phenyl, naphthyl, tetrahydronaphthyl, indanyl and the like; optionally substituted by 1 to 3 suitable substituents as defined above.

As used herein, the term "heteroaryl" refers to an aromatic heterocyclic group usually with one heteroatom selected from O, S and N in the ring. In addition to said heteroatom, the aromatic group may optionally have up to four N atoms in the ring. For example, heteroaryl group includes pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, and the like; optionally substituted by 1 to 3 suitable substituents as defined above which include but are not limited to fluoro, chloro, trifluoromethyl, (C$_1$-C$_6$)alkoxy, (C$_6$-C$_{10}$)aryloxy, trifluoromethoxy, difluoromethoxy or (C$_1$-C$_6$)alkyl.

The term "heterocyclic" as used herein refers to a cyclic group containing 1-9 carbon atoms and 1 to 4 hetero atoms selected from N, P, O, S(O), or NR. Examples of such rings include dioxaphosphorinane, azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, indolinyl, isoindolinyl, quinuclidinyl, chromanyl, isochromanyl, benzoxazinyl, and the like. Examples of said monocyclic saturated or partially saturated ring systems are 1,3,2-dioxaphosphorinane, tetrahydrofuran-2-yl, tetrahydrofuran-3-yl, imidazolidin-1-yl, imidazolidin-2-yl, imidazolidin-4-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, thiomorpholin-yl, 1,2-tetrahydrothiazin-2-yl, 1,3-tetrahydrothiazin-3-yl, tetrahydrothiadiazin-yl, morpholin-yl, 1,2-tetrahydrodiazin-2-yl, 1,3-tetrahydrodiazin-1-yl, 1,4-oxazin-2-yl, 1,2,5-oxathiazin-4-yl and the like; optionally containing 1 or 2 double bonds and optionally substituted by 1 to 3 suitable substituents as defined above which include but are not limited to fluoro, chloro, trifluoromethyl, $(C_1-C_6)$alkoxy, $(C_6-C_{10})$aryloxy, trifluoromethoxy, difluoromethoxy or $(C_1-C_6)$alkyl.

Nitrogen heteroatoms as used herein refers to —N═, >N and —NH; wherein —N═ refers to a nitrogen double bond; >N refers to a nitrogen containing two bond connections and —NH refers to a nitrogen containing one bond.

"Embodiment" as used herein refers to specific groupings of compounds or uses into discrete subgenera. Such subgenera may be cognizable according to one particular substituent such as a specific $R^1$ or $R^4$ group. Other subgenera are cognizable according to combinations of various substituents, such as all compounds wherein $R^2$ is hydrogen and $R^1$ is $(C_1-C_6)$alkyl.

As used herein, the terms "oil composition," "lubrication composition," "lubricating oil composition," "lubricating oil," "lubricant composition," "fully formulated lubricant composition," and "lubricant" are considered synonymous, fully interchangeable terminology referring to the finished lubrication product comprising a major amount of a base oil plus a minor amount of an additive composition.

As used herein, the terms "additive package," "additive concentrate," and "additive composition" are considered synonymous, fully interchangeable terminology referring to the portion of the lubricating composition excluding the major amount of base oil stock mixture.

As used herein, the terms "agent" and "additive" are considered synonymous, fully interchangeable terminology referring to any single functional component of a lubricating composition, excluding the major amount of base oil stock mixture.

Additional objects and advantages of the disclosure will be set forth in part in the description which follows, and/or may be learned by practice of the disclosure. The objects and advantages of the disclosure will be realized and attained by means of the elements and combinations particularly pointed out in the appended claims.

It is to be understood that both the foregoing general description and the following detailed description are exemplary and explanatory only and are not restrictive of the disclosure, as claimed.

DETAILED DESCRIPTION

The compounds of formula I can be prepared using the synthetic route outlined in Scheme I. The substituents in Scheme I have the same meaning as the substituents defined for formula I, with the exception that the $R^1$ substituent in formula I is represented in Scheme I as $R^1$, $R^{1'}$, and $R^{1''}$, as described more fully below.

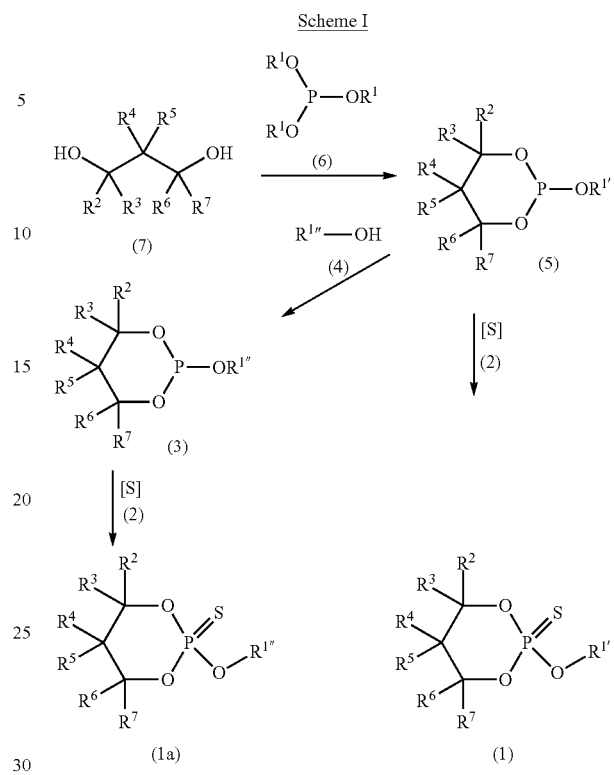

Scheme I

From Scheme I, compounds of formula (1) and (1a) can be prepared by reacting a 1,3-diol (7), optionally substituted at the $R^1$ or $R^1$, $R^2$, $R^3$, $R^4$, $R^5$, $R^6$ and $R^7$ positions, with a phosphite compound of the general formula $P(OR^1)_3$ (6), typically a trialkyl phosphite, such as, for example, triethyl or trimethyl phosphite, to produce a cyclic phosphite, a 1,3,2-dioxaphosphorinane compound (5). Under equal molar reaction conditions, compounds (7) and (6) react to yield as the major product, 1,3,2-dioxaphosphorinane compounds, where $R^{1'}$ of compound 5 is provided by the $R^1$ functionality of the phosphite compound 6. However, when the diol compound (7) is provided in excess, for example a 3:2 ratio, the major product is a 1,3,2-dioxaphosphorinane compound where the $R^{1'}$ functionality of compound 5 is provided by the diol compound (7). The 1,3,2-dioxaphosphorinane compound (5) is subsequently reacted with a sulfur source (2), typically elemental sulfur or an organic sulfur compound such as sulfurized isobutylene (SIB) to yield thiophosphate compounds, generally classed as 2-sulfide-1,3,2-dioxaphosphorinane compounds, compound (I).

Alternatively, the 1,3,2-dioxaphosphorinane compound (5) may be further reacted with an alcohol compound of the general formula R1"-OH (4), for example a long-chain alcohol, such as oleyl alcohol, in a transesterification reaction to introduce functionality at the $R^{1'}$ position of the 1,3,2-dioxaphosphorinane compound (5). The new 1,3,2-dioxaphosphorinane compound, compound (3), retains the $R^{1''}$ functionality of the alcohol (4). The 1,3,2-dioxaphosphorinane compound (3) can be subsequently reacted with a sulfur source (2) to yield the 2-sulfide-1,3,2-dioxaphosphorinane compound, compound (1a).

In some embodiments, one or more compounds according to formula I, or a tribologically acceptable salt or solvate thereof may be incorporated into a lubricating composition. A lubricant additive composition may be prepared comprising one or more compounds according to formula I, or a tribologically acceptable salt or solvate thereof. A lubricant composition may comprise a) a major amount of a base oil; and b) a minor amount of an additive composition comprising one or more compounds of formula I, or a tribologically acceptable salt or solvate thereof.

Optional Additive Components

In another aspect of the present disclosure, the compounds of formula I may be formulated into an additive composition and blended with a base oil to obtain a lubricating fluid. Such a fluid may be formulated optionally with one or more selected ingredients and additives that include, without limitation, those described hereinbelow. Such additives may include, but are not limited to, air expulsion additives, antifoamants (foam inhibitors), antioxidants, anti-rust additives, antiwear additives, colorants, corrosion inhibitors, dispersants, extreme pressure agents, friction modifiers, metal deactivators, metallic detergents, organic phosphorus compounds, pour point depressants, seal swell agents, and/or viscosity index improvers. Additives are generally described in C. V. Smalheer et al., Lubricant Additives, pages 1-11 (1967) and in U.S. Pat. No. 4,105,571, among others. The supplemental additives include those that are commercially available.

Suitable oil-soluble ashless dispersants may be selected from the group consisting of: a succinimide dispersant, a succinic ester dispersant, a succininic ester-amide dispersant, a Mannich base dispersant, phosphorylated forms thereof, boronated forms thereof, and phosphorylated and boronated forms thereof.

In selecting any of the optional additives, it may be important to ensure that the selected component(s) may be soluble or stably dispersible in the additive package and the finished lubricant composition, and may be compatible with the other components of the composition. By preference, a person skilled in the art may be expected to choose an additional optional additive or combination of additives, amounts thereof, such that the performance properties of the composition, such as the improved extreme pressure or thermal stability performance, among other properties, needed or desired, as applicable, in the overall finished composition, may not be substantially adversely affected.

In general, the ancillary additive components may be employed in the lubricating oil in minor amounts sufficient to improve the performance characteristics and properties of the base fluid. The amounts may thus vary in accordance with such factors as the viscosity characteristics of the base fluid employed, the viscosity characteristics desired in the finished fluid, the service conditions for which the finished fluid is intended, and the performance characteristics desired in the finished fluid.

However, generally speaking, the following general concentrations (weight percent unless otherwise indicated) of the additional components in the base fluids may be illustrative.

Respective amounts of additives may be blended into a selected base oil in amounts that may be sufficient to provide their expected performance. An effective amount for a specific formulation may be readily ascertained, but for illustrative purposes these general guides for representative effective amounts are provided. The amounts below are given in weight % of the fully formulated lubricating fluid.

| Component | Example Ranges 1 and 2 (wt %) | |
|---|---|---|
| Antiwear Compound | 0-10 | 0.3-6 |
| Dispersant | 0-20 | 2-8 |

-continued

| Component | Example Ranges 1 and 2 (wt %) | |
|---|---|---|
| EP Agent | 0-5 | 2-4 |
| Rust inhibitor | 0-1.5 | 0.05-1.0 |
| Corrosion Inhibitor | 0-5 | 0.05-3 |
| Demulsifier | 0-5 | 0.005-1.0 |
| Antifoam Agent | 0-0.5 | 0.001-0.1 |
| Diluent | 0-10 | 1.0-5.0 |
| Lubricating Base Oil | Balance | |

It will be appreciated that the individual components employed may be separately blended into the base fluid or may be blended therein in various sub-combinations, if desired. Ordinarily, the particular sequence of such blending steps is not crucial. Moreover, such components may be blended in the form of separate solutions in a diluent. It may be preferable, however, to blend the additive components used in the form of a concentrate, as this simplifies the blending operations, reduces the likelihood of blending errors, and takes advantage of the compatibility and solubility characteristics afforded by the overall concentrate.

Additive concentrates may thus be formulated to contain all of the additive components and if desired, some of the base oil component, in amounts proportioned to yield finished fluid blends consistent with the concentrations described above. In most cases, the additive concentrate will contain one or more diluents such as light mineral oils, to facilitate handling and blending of the concentrate. Thus concentrates containing up to about 50 wt. % of one or more diluents or solvents may be used, provided the solvents are not present in amounts that interfere with the low and high temperature and flash point characteristics and the performance of the finished power transmission fluid composition. In this regard, the additive components used pursuant to this disclosure may be selected and proportioned such that an additive concentrate or package formulated from such components will have a flash point of about 170° C. or above, using the ASTM D-92 test procedure.

SYNTHESIS EXAMPLES

Example A

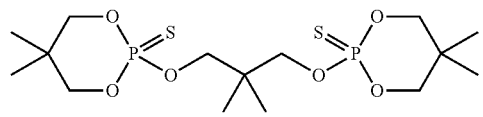

In the preparation of 2,2'-[(2,2-dimethyl-1,3-propanediyl)bis(oxy)]-bis(5,5-dimethyl-,1,3,2-dioxaphosphorinane), a 1 L reactor equipped with a thermocouple, distillation column, mechanical stirrer, and a 1 L round bottom receiving flask, was charged with triethyl phosphite (500 g) and neopentyl glycol (448 g). The mixture was heated to 100° C. to 120° C. for 3 hours under atmospheric pressures and then for 2 hours under reduced pressure, allowing low boiling by-products to be distilled off. The resulting material contained a major proportion of 2,2'-[(2,2-dimethyl-1,3-propanediyl)bis(oxy)]-bis(5,5-dimethyl-,1,3,2-dioxaphosphorinane).

To sulfurize 2,2'-[(2,2-dimethyl-1,3-propanediyl)bis(oxy)]-bis(5,5-dimethyl-,1,3,2-dioxaphosphorinane) using elemental sulfur as the sulfur source, in a 1 L reactor, a mixture containing 2,2'-[(2,2-dimethyl-1,3-propanediyl)bis (oxy)]bis(5,5-dimethyl-,1,3,2-dioxaphosphorinane) (471 g) was heated to 90° C. under nitrogen. Sulfur was added to the reactor and then the mixture was heated to 90° C. to 130° C. for 8 hours resulting in a white solid containing a major portion of 2,2'-sulfide-2,2'-[(2,2-dimethyl-1,3-propanediyl) bis(oxy)]-bis(5,5-dimethyl-,1,3,2-dioxaphosphorinane).

As an alternative, in situ sulfurization of 2,2'-[(2,2-dimethyl-1,3-propanediyl)bis(oxy)]-bis(5,5-dimethyl-,1,3,2-dioxaphosphorinane) may use sulfurized isobutylene (SIB) as the sulfur source. In a lubricating composition, 2,2'-[(2,2-dimethyl-1,3-propanediyl)bis(oxy)]bis(5,5-dimethyl-,1,3,2-dioxaphosphorinane) was heated in the presence of excess sulfurized isobutylene at 60° C. for 1 hour. A major portion of the starting dioxaphosphorinane was sulfurized to 2,2'-sulfide-2,2'-[(2,2-dimethyl-1,3-propanediyl)bis(oxy)]-bis(5,5-dimethyl-,1,3,2-dioxaphosphorinane) as observed in P-31 NMR analyses of the lubricating composition.

Example B

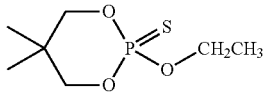

In the preparation of 2-ethoxy-5,5-dimethyl-1,3,2-dioxaphosphorinane, a 1 L reactor equipped with a thermocouple, distillation column, mechanical stirrer, and a 1 L round bottom receiving flask, was charged with triethyl phosphite (600 g) and neopentyl glycol (376 g). The mixture was heated to 100° C. to 110° C. for 3 hours under atmospheric pressures and then for 2 hours under reduced pressure, allowing low boiling by-products to be distilled off. The resulting material contained a major proportion of 2-ethoxy-5,5-dimethyl-1,3,2-dioxaphosphorinane.

In situ sulfurization of 2,2'-[(2,2-dimethyl-1,3-propanediyl)bis(oxy)]bis(5,5-dimethyl-,1,3,2-dioxaphosphorinane) may use sulfurized isobutylene as the sulfur source. In a lubricating composition, 2-ethoxy-5,5-dimethyl-1,3,2-dioxaphosphorinane was heated in the presence of excess sulfurized isobutylene at 60° C. for 1 hour. A major portion of the starting dioxaphosphorinane was sulfurized to 2-sulfide-2-ethoxy-5,5-dimethyl-1,3,2-dioxaphosphorinane as observed in P-31 NMR analyses of the lubricating composition.

Example C

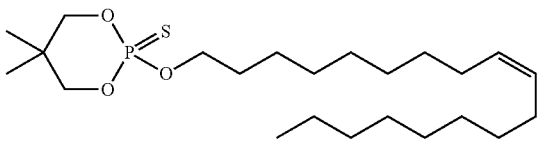 [SMILES: CCCCCCCC/C=C\CCCCCCCCOP1(=S)OCC(C)(C)CO1]

In the preparation of 2-oleoxy-5,5-dimethyl-1,3,2-dioxaphosphorinane, a 1 L reactor equipped with a thermocouple, distillation column, mechanical stirrer, and a 1 L round bottom receiving flask, was charged with triethyl phosphite (600 g) and neopentyl glycol (376 g). The mixture was heated to 100° C. to 110° C. for 3 hours under atmospheric pressures and then for 2 hours under reduced pressure, allowing low boiling by-products to be distilled off. The resulting material contained a major proportion of 2-ethoxy-5,5-dimethyl-1,3,2-dioxaphosphorinane.

In a separate 1 L reactor, 267 g of 2-ethoxy-5,5-dimethyl-1,3,2-dioxaphosphorinane was heated to 100° C. in the presence of 400 g of oleyl alcohol for 3 hours under reduced pressure. During this procedure, low boiling by-products were distilled off. The resulting material contained a major portion of 2-oleoxy-5,5-dimethyl-1,3,2-dioxaphosphorinane.

In situ sulfurization of 2-oleoxy-5,5-dimethyl-1,3,2-dioxaphosphorinane may use sulfurized isobutylene as the sulfur source. In a lubricating composition, 2-oleoxy-5,5-dimethyl-1,3,2-dioxaphosphorinane was heated in the presence of excess sulfurized isobutylene at 60° C. for 1 hour. A major portion of the starting dioxaphosphorinane was sulfurized to 2-sulfide-2-oleoxy-5,5-dimethyl-1,3,2-dioxaphosphorinane as observed in P-31 NMR analyses of the lubricating composition.

Example D

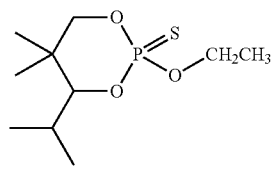

A 500 mL reactor equipped with a thermocouple, distillation column, mechanical stirrer and a 1 L round bottom receiving flask, was charged with triethyl phosphite (134 g) and 2,2,4-trimethyl-1,3-pentane-diol (118 g). The pressure in the system was reduced to below 100 mmHg and then increased back to atmospheric pressure with nitrogen. The mixture was heated to 80° C. to 105° C. for 3 hrs under atmospheric pressures and then for 2 hrs under reduced pressure (−28 in Hg), allowing low boiling by-products to be distilled off. The resulting material contained a major proportion of 2-ethoxy-4-isopropyl-5,5-dimethyl-1,3,2-dioxaphosphorinane.

In a lubricating composition, 2-ethoxy-4-isopropyl-5,5-dimethyl-1,3,2-dioxaphosphorinane was heated in the presence of excess sulfurized isobutylene at 60° C. for 1 hr. A major portion of the starting dioxaphosphorinane was sulfurized to 2-sulfide-2-ethoxy-4-isopropyl-5,5-dimethyl-1,3,2-dioxaphosphorinane as observed in P-31 NMR analyses of the lubricating composition.

Example E

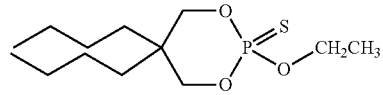 [SMILES: CCCCC1(CCCC)COP(=S)(OCC)OC1]

A 100 mL reactor equipped with a thermocouple, distillation column, and a 100 mL round bottom receiving flask, was charged with triethyl phosphite (18 g) and 2,2-dibutyl-1,3-propandiol (20 g). The pressure in the system was reduced to below 100 mmHg and then increased back to atmospheric pressure with nitrogen. The mixture was heated to 100° C. to 110° C. for 3 hrs under atmospheric pressures and then for 2 hrs under reduced pressure (−28 in Hg), allowing low boiling by-products to be distilled off. The resulting material contained a major proportion 2-ethoxy-5,5-dibutyl-1,3,2-dioxaphosphorinane.

In a lubricating composition, 2-ethoxy-5,5-dibutyl-1,3,2-dioxaphosphorinane was heated in the presence of excess sulfurized isobutylene at 60° C. for 1 hr. A major portion of the starting dioxaphosphorinane was sulfurized to 2-sulfide-2-ethoxy-5,5-dibutyl-1,3,2-dioxaphosphorinane as observed in P-31 NMR analyses of the lubricating composition.

Test Samples

Finished fluid test Samples A, B, C, D and E were prepared including anti-wear compounds according to Examples A, B, C, D and E, respectively. A sixth sample, test Sample F, was used as a control and did not include a phosphorus-containing anti-wear agent. The test samples were otherwise identical. Table 1 shows the test sample compositions.

TABLE 1

Test Sample Compositions

| Component | Concentration |
| --- | --- |
| Antiwear Example A, B, C, D, or E | 900 ppm Phosphorus |
| Group I Base Oil | 90-93 wt % |
| Sulfurized isobutylene (SIB) Extreme Pressure Agent | 3.5 wt % |
| Amine Rust Inhibitor(s) | 0.5 wt % |
| Corrosion Inhibitor(s) | 0.15 wt % |
| Demulsifier | 0.01 wt % |
| Dispersant | 1.3 wt % |
| Anti-Foamant | 0.04 wt % |
| Diluent | 1.6 wt % |

Tests

Samples A, B, C, D, E, and F were subjected to the L-37 Test Green (according to ASTM D6121). The L-37 Test Green measures a lubricant's ability to protect final drive axles from abrasive wear, adhesive wear, plastic deformation, and surface fatigue when subjected to low-speed, high torque conditions. Lack of protection may lead to premature gear and/or bearing failure. After the test is completed, the ring gear, pinion, and pinion meeting are removed from the gear set and rated. Passing conditions for this test are given in Table 2.

TABLE 2

ASTM D6121 (L-37) Test Green Passing Conditions

| Observation | Passing Rating (10 Max) |
| --- | --- |
| Broken Teeth | NO |
| Wear | >5 |
| Rippling | >8 |
| Ridging | >8 |
| Pitting/Spelling | >9.3 |
| Scoring | 10 |

Each of the finished fluid Samples A, B, C, D, E, and F were run in a green L-37 test according to ASTM D6121. At the end of the test, the gear set was rated according to ASTM D6121. Samples A, B, C, D and E gave passing results and demonstrated the utility of Examples A, B, C, D and E as anti-wear components in a typical gear oil (Table 3).

TABLE 3

L-37 Test Results

| | Sample A | Sample B | Sample C | Sample D | Sample E | Sample F |
| --- | --- | --- | --- | --- | --- | --- |
| Pass/Fail | Pass | Pass | Pass | Pass | Pass | Fail |
| Wear | 7 | 9 | 8 | 8 | 8 | 4 |
| Rippling | 10 | 10 | 10 | 10 | 10 | 5 |
| Ridging | 10 | 10 | 9 | 10 | 10 | 7 |
| Pitting/Spalling | 9.9 | 10 | 9.9 | 9.9 | 10 | 7 |
| Scoring | 10 | 10 | 10 | 10 | 10 | 10 |

It is understood that lubricant compositions and/or lubricant additives according to an embodiment of the present disclosure may further exhibit sufficient thermal stability in anti-wear performance.

At numerous places throughout this specification, reference has been made to a number of U.S. patents, European Patent Applications (published), PCT International patent publications, and literature references. All such cited documents are expressly incorporated in full into this disclosure as if fully set forth herein.

As used throughout the specification and claims, "a" and/or "an" may refer to one or more than one. Unless otherwise indicated, all numbers expressing quantities of ingredients, properties such as molecular weight, percent, ratio, reaction conditions, and so forth used in the specification and claims are to be understood as being modified in all instances by the term "about." Accordingly, unless indicated to the contrary, the numerical parameters set forth in the specification and claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

While the present disclosure has been principally demonstrated hereinabove in the examples as a gear fluid having improved gear antiwear, it is contemplated that the benefits of the fluid embodiment are similarly applicable to other lubricating fluids. Included within the scope of the present disclosure may be, but not limited to, gear oils, hydraulic fluids, engine oils, heavy duty hydraulic fluids, industrial oils, power steering fluids, pump oils, tractor fluids, and universal tractor fluids. Apparatus embodiments may include, but are not limited to, gears, engines, hydraulic mechanisms, power steering devices, pumps and the like incorporating a lubricating fluid according to the present disclosure.

Other embodiments of the present disclosure will be apparent to those skilled in the art from consideration of the specification, Figure 1 and practice of the embodiments disclosed and suggested herein. It is intended that the specification and examples be considered as exemplary only, with a true scope and spirit of the disclosure being indicated by the following claims.

What is claimed is:

1. A method of making a lubricant additive, comprising:
reacting a 1,3-diol with a trialkyl phosphite to form a 1,3,2-dioxaphosphorinane; and
reacting the 1,3,2-dioxaphosphorinane with elemental sulfur or an organic sulfur compound to form a 2-sulfide-1,3,2-dioxaphosphorinane.

2. A method of making a lubricant additive, comprising:
reacting a 1,3-diol with a trialkyl phosphite to form a 1,3,2-dioxaphosphorinane;
reacting the 1,3,2-dioxaphosphorinane with an alcohol to form a reaction product; and
reacting the reaction product with elemental sulfur or an organic sulfur compound to form a 2-sulfide-1,3,2-dioxaphosphorinane.

* * * * *